United States Patent
Onuma et al.

(10) Patent No.: US 10,251,670 B2
(45) Date of Patent: Apr. 9, 2019

(54) POSITIONING APPARATUS

(71) Applicants: CANON U.S.A., INC., Melville, NY (US); THE BRIGHAM AND WOMEN'S HOSPITAL INC., Boston, MA (US); Kazufumi Onuma, Kawasaki-shi (JP); Sang-Eun Song, Chestnut Hill, MA (US)

(72) Inventors: Kazufumi Onuma, Kawasaki (JP); Sang-Eun Song, Chestnut Hill, MA (US)

(73) Assignees: Canon U.S.A., Inc., Melville, NY (US); The Brigham and Women's Hospital, Boston, MA (US)

( * ) Notice: Subject to any disclaimer, the term of this patent is extended or adjusted under 35 U.S.C. 154(b) by 200 days.

(21) Appl. No.: 15/309,062

(22) PCT Filed: May 8, 2015

(86) PCT No.: PCT/US2015/029837
§ 371 (c)(1),
(2) Date: Nov. 4, 2016

(87) PCT Pub. No.: WO2015/171988
PCT Pub. Date: Nov. 12, 2015

(65) Prior Publication Data
US 2017/0071626 A1 Mar. 16, 2017

Related U.S. Application Data (60) Provisional application No. 61/991,059, filed on May 9, 2014.

(51) Int. Cl.
*A61B 90/11* (2016.01)
*A61B 17/34* (2006.01)
(Continued)

(52) U.S. Cl.
CPC ...... *A61B 17/3403* (2013.01); *A61B 10/0233* (2013.01); *A61B 90/11* (2016.02);
(Continued)

(58) Field of Classification Search
CPC ..... A61B 90/10; A61B 90/11; A61B 17/3403; A61B 2017/3407; A61B 2017/3409
See application file for complete search history.

(56) References Cited

U.S. PATENT DOCUMENTS

| 4,841,967 A | 6/1989 | Chang et al. |
|---|---|---|
| 5,116,344 A | 5/1992 | Sundqvist |

(Continued)

FOREIGN PATENT DOCUMENTS

| CA | 2784988 A1 | 2/2013 |
|---|---|---|
| EP | 2561821 A1 | 2/2013 |

(Continued)

OTHER PUBLICATIONS

U.S. Office Action issue in U.S. Appl. No. 14/799,021 dated Dec. 22, 2016.
(Continued)

*Primary Examiner* — Kathleen Holwerda
(74) *Attorney, Agent, or Firm* — Canon USA Inc., IP Division (57) ABSTRACT

A positioning apparatus includes a needle guide, a rotation unit, a detector for the rotation position, a position measuring unit, an engageable stopper, and a setting unit for setting position information to a value corresponding to a predetermined position are provided herewith. The positioning apparatus can be used, for example, to position a needle placement manipulator.

21 Claims, 11 Drawing Sheets

(51) Int. Cl.
*A61B 90/00* (2016.01)
*A61B 10/02* (2006.01)
(52) U.S. Cl.
CPC ....... *A61B 90/37* (2016.02); *A61B 2017/3407* (2013.01); *A61B 2017/3409* (2013.01); *A61B 2090/374* (2016.02)

(56) References Cited

U.S. PATENT DOCUMENTS

| | | | |
|---|---|---|---|
| 5,196,019 A | 3/1993 | Davis et al. | |
| 5,201,742 A | 4/1993 | Hasson | |
| 5,280,427 A | 1/1994 | Magnusson et al. | |
| 5,682,892 A * | 11/1997 | Selder .................. | A61B 90/11 324/318 |
| 5,957,934 A | 9/1999 | Rapoport | |
| 6,079,681 A | 6/2000 | Stern et al. | |
| 6,119,032 A | 9/2000 | Martin et al. | |
| 6,185,445 B1 | 2/2001 | Knuttel | |
| 6,413,263 B1 | 7/2002 | Lobdill et al. | |
| 6,676,669 B2 | 1/2004 | Charles et al. | |
| 7,022,082 B2 | 4/2006 | Sonek | |
| 7,083,608 B2 | 8/2006 | Tomita et al. | |
| 7,187,104 B2 | 3/2007 | Yamamoto et al. | |
| 7,379,769 B2 | 5/2008 | Piron et al. | |
| 7,636,596 B2 | 12/2009 | Solar | |
| 7,824,417 B2 | 11/2010 | Magnusson et al. | |
| 8,241,301 B2 | 8/2012 | Zhang et al. | |
| 8,298,245 B2 | 10/2012 | Li et al. | |
| 8,308,740 B2 | 11/2012 | Tolley et al. | |
| 8,744,552 B2 | 6/2014 | Akuzawa et al. | |
| 9,222,996 B2 | 12/2015 | Fujimoto et al. | |
| 2001/0000940 A1 | 5/2001 | Maruyama | |
| 2002/0019641 A1 | 2/2002 | Truwit | |
| 2003/0107299 A1 | 6/2003 | Fujimoto | |
| 2004/0064148 A1 | 4/2004 | Daum et al. | |
| 2005/0216026 A1 | 9/2005 | Culbert | |
| 2005/0261581 A1 | 11/2005 | Hughes et al. | |
| 2006/0149147 A1 | 7/2006 | Yanof | |
| 2006/0229641 A1 | 10/2006 | Gupta et al. | |
| 2007/0276407 A1 | 11/2007 | Vogele | |
| 2008/0004481 A1 | 1/2008 | Bax et al. | |
| 2008/0161829 A1 | 7/2008 | Kang | |
| 2008/0167663 A1 | 7/2008 | De Mathelin et al. | |
| 2008/0171930 A1 | 7/2008 | Abolfathi et al. | |
| 2009/0079431 A1 | 3/2009 | Piferi et al. | |
| 2009/0234369 A1 | 9/2009 | Bax et al. | |
| 2010/0010505 A1 | 1/2010 | Herlihy et al. | |
| 2010/0082040 A1 | 4/2010 | Sahni | |
| 2011/0190787 A1 | 8/2011 | Sahni | |
| 2011/0251624 A1 | 10/2011 | Yi et al. | |
| 2012/0016316 A1 | 1/2012 | Zhuang et al. | |
| 2012/0022368 A1 | 1/2012 | Brabrand et al. | |
| 2013/0069651 A1 | 3/2013 | Luminani | |
| 2013/0267834 A1 | 10/2013 | McGee | |
| 2013/0345718 A1 | 12/2013 | Crawford et al. | |
| 2014/0052154 A1 | 2/2014 | Griffiths et al. | |
| 2014/0121675 A1 | 5/2014 | Bax et al. | |
| 2014/0128881 A1 | 5/2014 | Tyc | |
| 2014/0128883 A1 | 5/2014 | Piron et al. | |
| 2014/0200445 A1 | 7/2014 | Boezaart et al. | |
| 2014/0275978 A1 | 9/2014 | Fujimoto et al. | |
| 2014/0275979 A1 | 9/2014 | Fujimoto et al. | |
| 2014/0336670 A1 | 11/2014 | Brabrand et al. | |
| 2014/0350572 A1 | 11/2014 | Elhawary et al. | |
| 2015/0238266 A1 | 8/2015 | Fujimoto et al. | |
| 2016/0074063 A1 | 3/2016 | Arimitsu et al. | |
| 2017/0014200 A1 | 1/2017 | Onuma et al. | |
| 2017/0030557 A1 | 2/2017 | Chen et al. | |

FOREIGN PATENT DOCUMENTS

| | | | | |
|---|---|---|---|---|
| JP | 2004320846 A | 11/2004 | | |
| JP | 2005083961 A | 3/2005 | | |
| JP | 2008237971 A | 10/2008 | | |
| WO | 2011146018 A1 | 11/2011 | | |
| WO | 2012178109 A1 | 12/2012 | | |
| WO | 2013084107 A2 | 6/2013 | | |
| WO | WO 2013084107 A2 * | 6/2013 | ........... | A61B 19/201 |
| WO | 2014152685 A1 | 9/2014 | | |
| WO | 2017/132505 A1 | 8/2017 | | |

OTHER PUBLICATIONS

U.S. Office Action issue in U.S. Appl. No. 13/836,708 dated Jan. 11, 2017.
U.S. Office Action issue in U.S. Appl. No. 13/836,708 dated Jun. 27, 2017.
U.S. Office Action issue in U.S. Appl. No. 14/632,991 dated Mar. 23, 2017.
Fischer, G. S.,et al., "MRI Guided Needle Insertion—Comparison of Four Technique", In Annual Scientific Conference of the Society of Interventional Radiology, 2006 (Abstract only).
Koethe, Y., et al., "Accuracy and efficacy of percutaneous biopsy and ablation using robotic assistance under aomputed tomography guidance: a phantom study", Eur Radiol., Nov. 13, 2013.
Perfint, Maxio Brochure: Planning and Targeting for CT guided Procedures.
Palmer, K., et al., "Development and evaluation of optical needle depth sensor for percutaneous diagnosis and therapies", Proc. of SPIE, Medical Imaging, 2014, vol. 9036.
PERFINT Inc Maxio Robot—Features http://www.perfinthealthcare.com/MaxioFeatures.asp Accessed Sep. 11, 2015.
Song, S.E., et al., "Biopsy Needle Artifact Localization in MRI-guided Robotic Transrectal Prostate Intervention", IEEE Trans Biomed Eng., Jul. 2012, pp. 1902-1911, vol. 59, No. 7.
Song, S.E., et al., "Design Evaluation of a Double ilng RCM Mechanism for Robotic Needle Guidance in MRI-guided Liver Interventions", IEEE/RSJ International Conference on Intelligent Robots and Systems (IROS), Nov. 3-7, 2013, pp. 4078-4083.
Hata, N., et al., "MRI-Compatible Manipulator with Remote-Center-of-Motion Control", J Magn Reson Imaging, May 2008, vol. 27, No. 5 http://www.ncbi.nlm.nih.gov/pmc/articles/PMC2815332/.

* cited by examiner

POSITIONING APPARATUS

CROSS-REFERENCE TO RELATED APPLICATION(S)

This application is a national stage application of PCT/US2015/029837 filed May 8, 2015 and claims priority from U.S. Provisional Application Ser. No. 61/991,059 filed May 9, 2014, the disclosure of each of which are hereby incorporated by reference herein in their entirety.

BACKGROUND OF THE INVENTION

Field of the Invention

The present invention relates to a positioning apparatus configured to perform a biopsy or therapy support by puncture using needle-shaped equipment.

Description of the Related Art

Demands for low invasion medicine are growing for improvement of quality of life (QOL) of patients in medical science. There have been developed percutaneous puncture therapies, such as a percutaneous puncture ablation therapy and a percutaneous puncture cryotherapy, as low invasion therapies.

However, since a portion which is the puncture target is not directly viewable in the percutaneous puncture therapies, a surgeon has to perform puncture based on medical images such as magnetic resonance imaging (MRI) or computed tomography (CT) or the like. A mechanism configured to assist puncture work such as described in U.S. Patent Pub. No. 2011/0190787 has been proposed as surgery support using medical images such as MRI or CT or the like. According to U.S. Patent Pub. No. 2011/0190787, a marker attached to a device is recognized on a medical image to obtain the posture of the device. Next, based on this posture and the position of the puncture target, the direction of puncture is determined to assist puncture work.

At this time, there is frequently assumed a case where the puncture direction is changed by the surgeon himself/herself in accordance with a scale. However, in the case of a scale for viewing, a visually recognizable scale is in the order of single degrees, and it is difficult to perform positioning with precision higher than that. Also, since it is difficult to add a numeric value to all factors of the scale, the surgeon has to count the number of scale factors at the time of performing positioning, which is a burden on the surgeon. Accordingly, in order to improve puncture accuracy and to reduce the burden on the surgeon, it is desirable to mount a position detector configured to detect not only the scale for viewing but also the position of the mechanism.

SUMMARY OF THE INVENTION

Though there does exist an absolute encoder capable of detecting an absolute position for some position detectors, this encoder needs complicated and high-precision signal processing. Therefore, reliability of the absolute position determination within a medical imaging device such as for MRI or CT or the like which is in a high-noise environment has not been thoroughly confirmed. Also, in the case of MRI, since a magnetic body such as an electric circuit or the like becomes a cause for distortion as to an image, increase in the circuit scale due to the absolute encoder may affect puncture accuracy. Accordingly, it is desirable to provide a device configured to perform positioning using a simple mechanism while securing puncture accuracy.

A positioning apparatus according an embodiment of the present invention may include: a guide configured to guide needle-shaped medical equipment in a longitudinal direction of the needle-shaped medical equipment; a rotation unit including the guide; a detector configured to detect change in the rotation position of the rotation unit to output the corresponding signal; a position measuring unit configured to output position information based on the signal output by the detector; a contact portion of the rotation unit; a stopper, which is engaged with the contact portion, configured to regulate the rotation of the rotation unit; and a setting unit configured to set the position information to a value corresponding to a predetermined position.

Further features of the present invention will become apparent from the following description of exemplary embodiments with reference to the attached drawings.

BRIEF DESCRIPTION OF THE DRAWINGS

Further objects, features and advantages of the present invention will become apparent from the following detailed description when taken in conjunction with the accompanying figures showing illustrative embodiments of the present invention.

FIGS. 15A and 15B are diagrams for describing another example of the stopper.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

DESCRIPTION OF THE EMBODIMENTS

First Embodiment

A first embodiment will be described with reference to FIGS. 1 to 11. First, description will be made regarding a mechanism configured to guide needle-shaped equipment (needle) of a medical support apparatus according to the present embodiment, and a method for changing an insertion direction thereof, with reference to FIG. 1, following which a configuration of home positioning with an incremental encoder will be described.

External View of Apparatus

First, the mechanism configured to guide the insertion direction of needle-shaped medical equipment will be descried. Note that, though a needle will be described as an example of needle-shaped medical equipment, it is also assumed to apply the present embodiment to medical equipment other than this. For example, the positioning apparatus as described herein may be used to guide other tubular-shaped diagnostic or surgical equipment.

There are bases 1a and 1b configured to be installed onto a puncture target. An annular first rotation member 2 (rotation mechanism 2) is attached to the base 1b. The first rotation member 2 is configured as a mechanism rotatable on the rotation axis perpendicular to the base 1b. Also, a second rotation member 3 (rotation mechanism 3) is installed onto the first rotation member 2. This second rotation member 3 is installed so as to have the rotation axis inclined a predetermined angle as to the rotation axis of the first rotation member 2. Though this inclination angle does not restrict the present invention in particular, let us exemplarily say that the second rotation member 3 inclines 15 degrees in the present embodiment. Also, the second rotation member 3 includes a guide mechanism 50 configured to regulate the insertion direction of needle-shaped equipment 5, which is assumed to have a hole shape as illustrated in FIG. 1 in the present embodiment.

Figure 1:
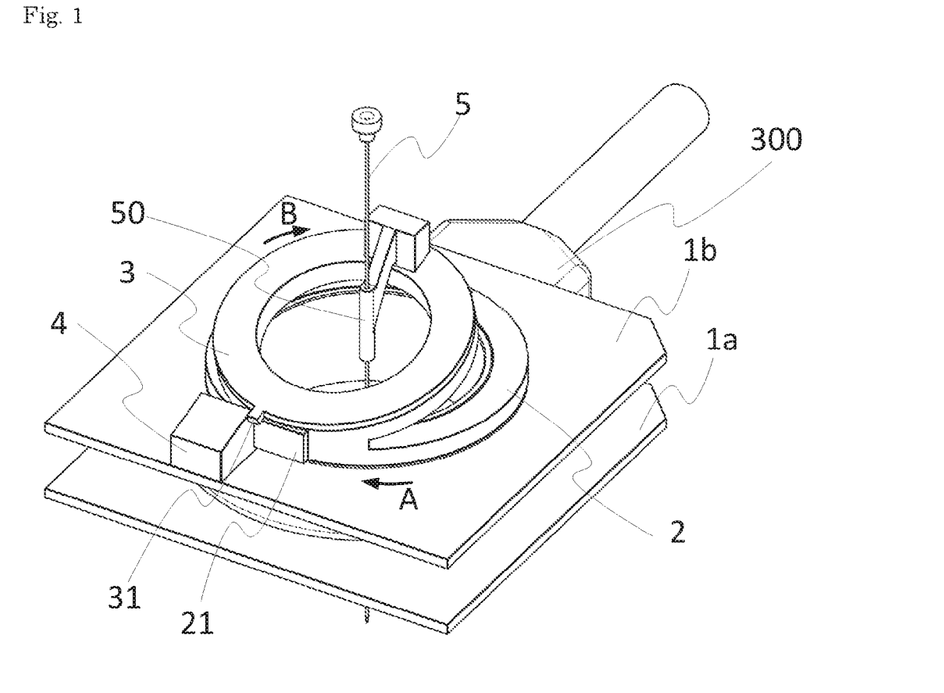
FIG. 1 is a diagram for describing a configuration of a mechanism according to a first embodiment.
Figure 2:
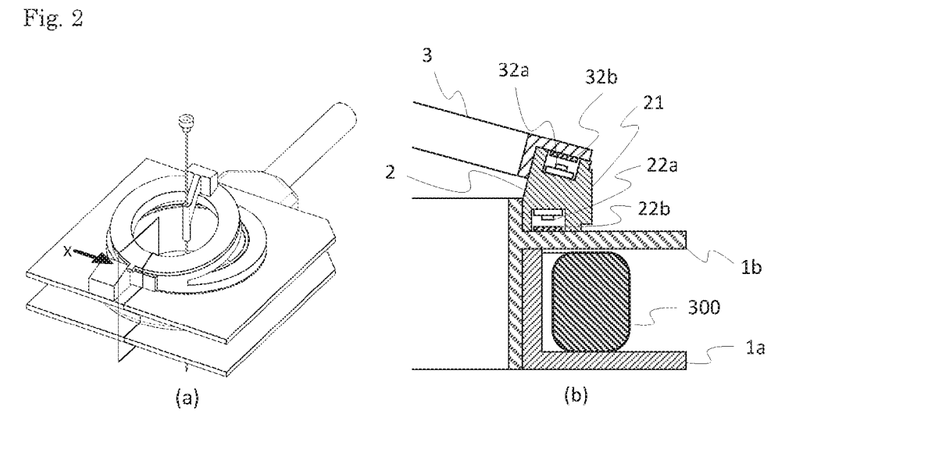
FIG. 2A is a diagram illustrating a cross section of the mechanism according to the first embodiment.
FIG. 2B is a cross-sectional view of the mechanism according to the first embodiment.

The insertion direction which is perpendicular in FIG. 1 can be inclined by rotating the second rotation member 3. Since the inclination angle of the second rotation member 3 is 15 degrees in the present embodiment, in the case of rotating the second rotation member 3 180 degrees, the insertion direction has the maximum inclination of 30 degrees. Also, though the inclination direction is gradually changed by rotating the second rotation member 3, the needle-shaped equipment 5 can be guided in an optional direction by synchronizing the rotation of the second rotation member 3 with the rotation of the first rotation member 2.

Computation of general inverse kinematics can be applied as a method for obtaining the angles of the first rotation member 2 and second rotation member 3 as to a target puncture position, and detailed description will be omitted here. Upon the target puncture position (the rotation positions of the first rotation member 2 and second rotation member 3) being informed to an operator, the operator rotates the first rotation member 2 and second rotation member 3, for example, by hand so that the informed target position agrees with the current position presented on a later-described presentation unit 14.

Detection Mechanism

A first position detector 22 configured to detect change in the rotation position of the first rotation member 2 as to the base 1b is provided between the base 1b and the first rotation member 2. Similarly, a second position detector 32 configured to detect change in the rotation position of the second rotation member 3 as to the first rotation member 2 is provided between the first rotation member 2 and the second rotation member 3. Detailed description will be made with reference to FIG. 2B which is a cross-sectional view in the cross section illustrated in FIG. 2A.

Optical elements 22a and 32a including a light source and a light-receiving unit are provided in the first rotation member 2. These optical elements 22a and 32a are fixed to the first rotation member 2, and are rotated along with the first rotation member 2. Also, an encoder scale 22b configured to read light at the optical element 22a is attached to the base 1b. Also, an encoder scale 32b configured to read light at the optical element 32a is attached to the second rotation member 3, and is rotated along with the second rotation member 3. These encoder scales are formed of an annular and radiate lattice having different reflectance ratios, as illustrated in FIG. 3.

Figure 3:
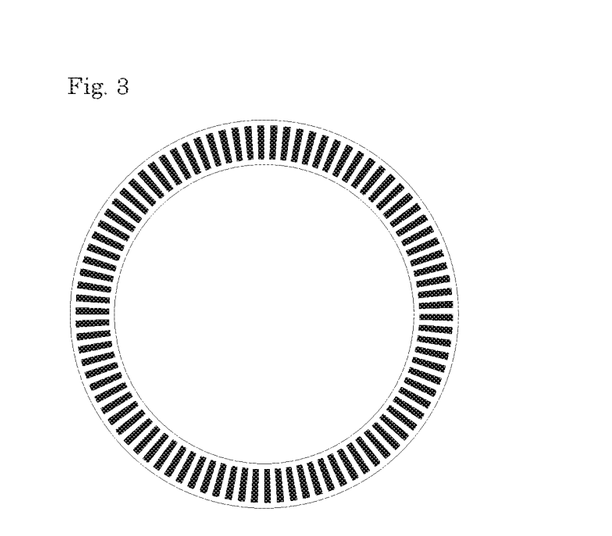
FIG. 3 is a diagram for describing an example of an encoder scale.

FIG. 3 schematically represents an encoder scale for description, and actually, the interval of the lattices has to be set finely in accordance with resolution needed. These first and second position detectors are both pulse-output type incremental encoders. The position detectors include two or more light-receiving elements at the light-receiving unit, and these light-receiving elements are provided so as to have phase difference in the circumferential direction as to the encoder scale. The position detectors output a pulse signal with equal to or greater than two phases indicating the amount of received light at the light-receiving elements. This two-phase pulse signal has phase difference based on the installation positions of the light-receiving elements, and lead/delay of the phases thereof is changed according to the direction of position changing. The pulse signal here is equivalent to a signal corresponding to change in the rotation position of the rotation member. The current position is updated based on this pulse signal, and is presented at a later-described presentation unit 14.

Figure 4:
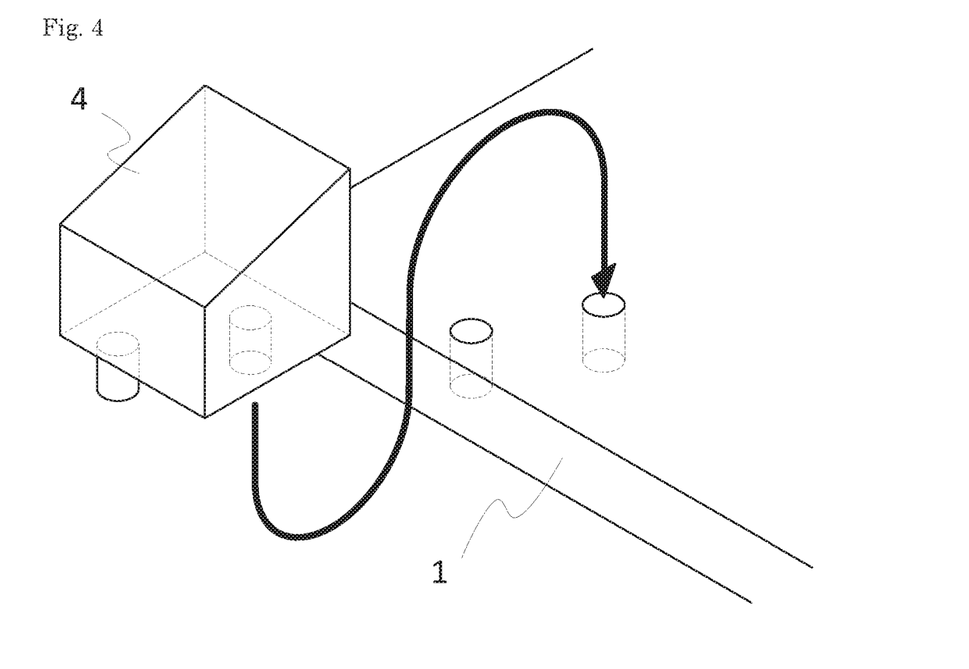
FIG. 4 is a diagram for describing an example of a stopper attachment mechanism.
Figure 5:
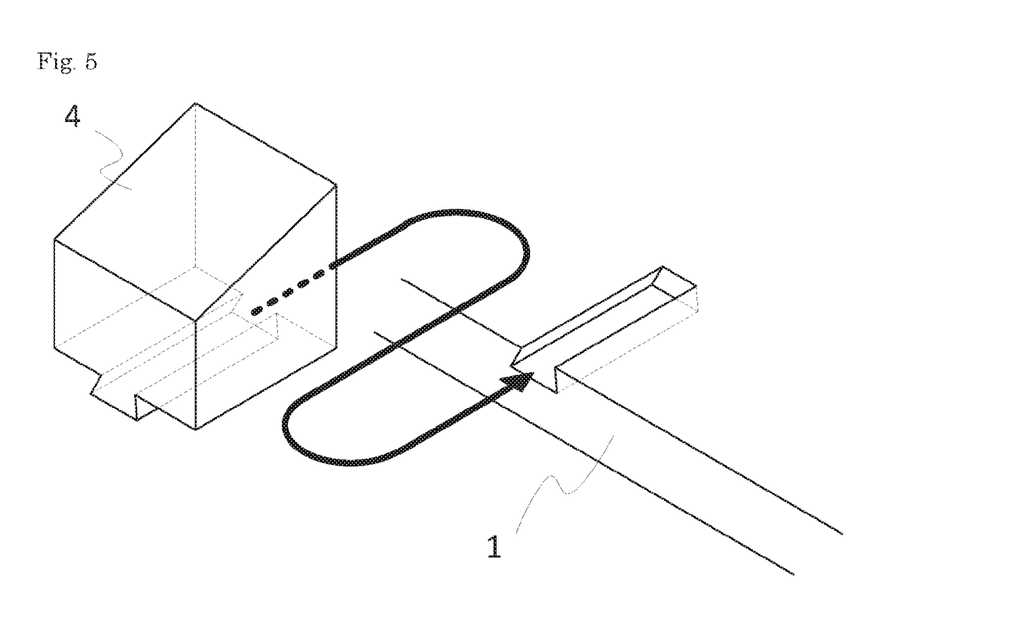
FIG. 5 is a diagram for describing another stopper attachment mechanism.

Next, a stopper 4 is provided to the base 1, and this stopper 4 is positioned in the base 1b by an uneven shape (engagement portion with a pin and a hole shape) such as illustrated in FIG. 4. Also, the stopper 4 may be pulled out in the vertical direction. There is a locus (space) defined by the movement of the first contact portion and second contact portion when the first rotation member 2 and second rotation member 3 are rotated. This pull-out of the stopper 4 suppresses the stopper 4 and the locus of each contact portion from crossing in space. In addition to the example illustrated in FIG. 4, the stopper 4 may be a slot-shaped engagement portion such as illustrated in FIG. 5, and have a shape to be pulled out in the horizontal direction at the time of attachment or detachment. Even the configuration illustrated in FIG. 5 enables the position of the stopper 4 to be accurately determined and also to be detached.

Also, a first contact portion 21 with a protruding shape is provided to the first rotation member 2, and is capable of being engaged with the stopper 4 attached to the base 1 by rotating the first rotation member 2 in an arrow-A direction. Thus, the first rotation member 2 can be positioned in a predetermined position. Similarly, a second contact portion 31 with a protruding shape is also provided to the second rotation member 3, and is capable of being engaged with the stopper 4 by rotating the second rotation member 31 in an arrow-B direction, in a state where the first contact portion 21 is engaged with the stopper 4. Thus, the second rotation member 3 can be positioned in a predetermined position.

Figure 6:
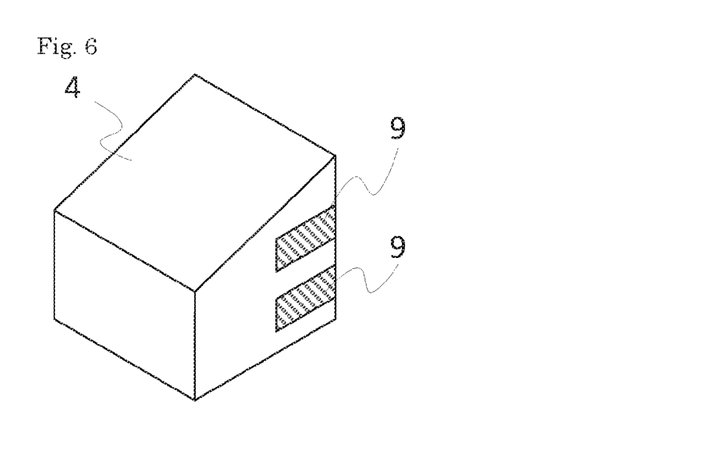
FIG. 6 is a diagram for describing an example of an attachment position of a rotation regulation detecting unit.

Also, as illustrated in FIG. 6, a rotation regulation detecting unit 9 is provided to the stopper 4, which detects that the first rotation member 2 and second rotation member 3 are regulated in a predetermined rotation position. It is desirable to provide a pressure sensor or contact sensor to the contact surface of the stopper 4 as illustrated in FIG. 6 as the rotation regulation detecting unit 9.

Figure 7:
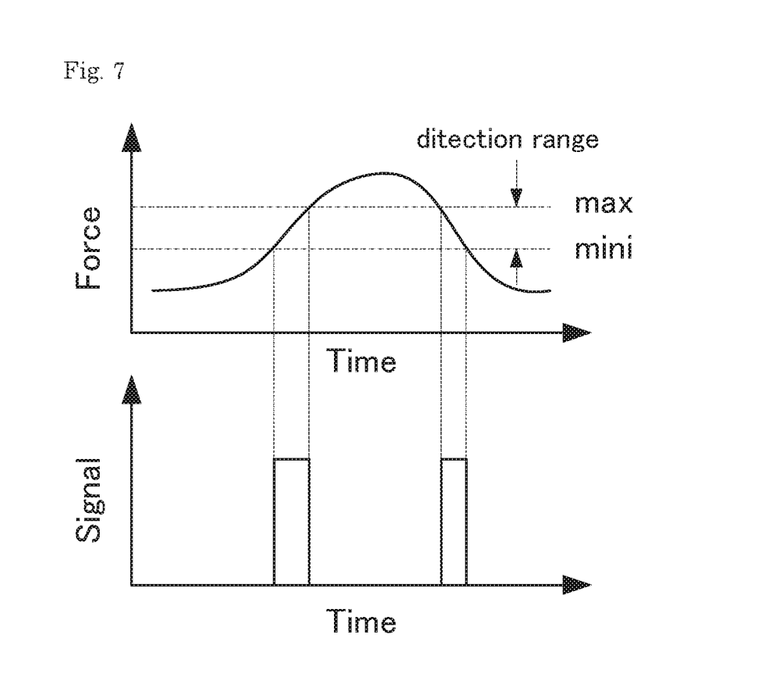
FIG. 7 is a diagram for describing an example of a rotation regulation detecting unit with a pressure sensor.

For example, in the case of the pressure sensor, it is desirable to output a signal for determining that rotation is regulated only when detecting pressure within a predetermined contact pressure range as illustrated in FIG. 7. Thus, reproducibility of positioning is improved.

Figure 8:
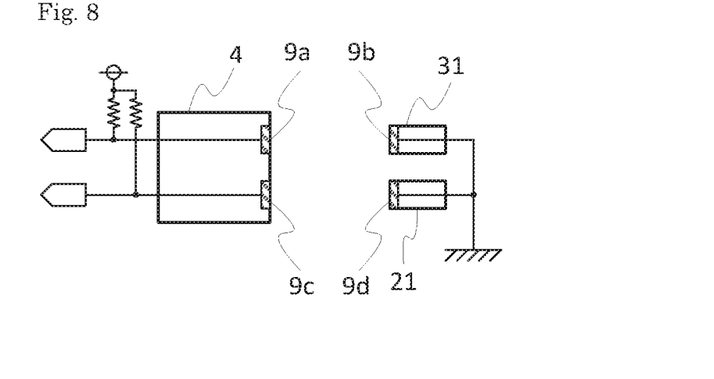
FIG. 8 is a diagram for describing an example of a rotation regulation detecting unit with a contact sensor.
Figure 9:
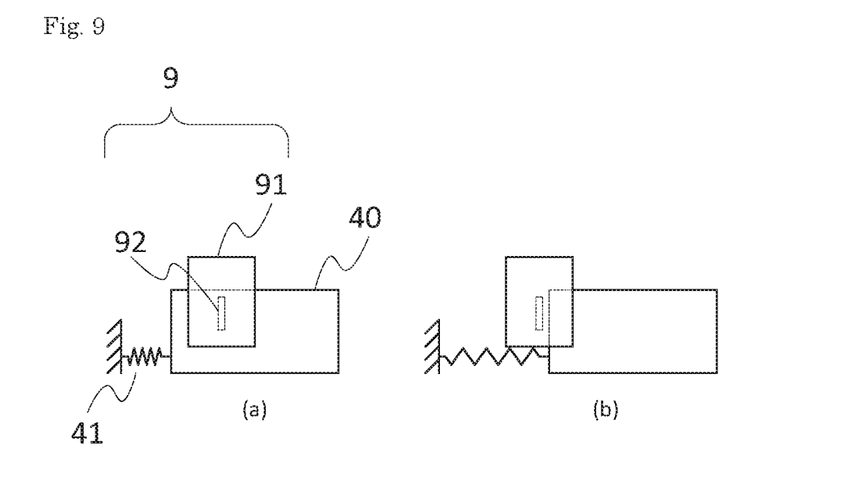
FIGS. 9A and 9B are diagrams for describing an example of a rotation regulation detecting unit with a photo interrupter.

Also, a simple example for realizing the contact sensor can be realized as a simple switch by providing electrodes 9a, 9b, 9c, and 9d onto the contact surface using a circuit as illustrated in FIG. 8. At this time, since the detection signal exhibit chattering, it is desirable to provide a filter circuit configured to remove chattering.

In the case that the stopper 4 is configured of a protruding portion and an elastic member such as illustrated in later-described FIGS. 15A to 18D', a photo interrupter 91 may additionally be employed as illustrated in FIGS. 9A and 9B. In this case, when a protruding portion 40 of the stopper 4 protrudes, the protruding portion 40 passes through a detecting unit 92 of the photo interrupter 91, whereby it can be detected that the rotation of the rotation member is regulated.

Also, the rotation regulation detecting unit 9 does not necessarily have to be configured to output a signal to the effect that the rotation of each of the first rotation member 2 and second rotation member 3 is regulated, and may be configured to output a signal only when both of the two rotation members are regulated. In this case, when the signal is input from the rotation regulation detecting unit 9, a position information setting unit 10 has to be configured to update both of the position information of the two rotation members to a predetermined value.

Also, the rotation regulation detecting unit 9 does not necessarily have to be provided to the stopper 4, and may be provided to the contact portions 21 and 31 of each rotation member, for example. Also, the rotation regulation detecting unit 9 itself does not necessarily have to be employed. For example, a mechanical switch (pressing portion) configured to instruct the same signal output as signal output from the rotation regulation detecting unit 9 may be provided to the apparatus. An arrangement may be made wherein the user moves a rotation member by hand, the contact portions 21 and 31 are engaged with the stopper 4 at this time, and when confirming that the rotation of the rotation member is regulated and stopped, the user is allowed to operate the switch thereof.

System Block Diagram

Figure 10:
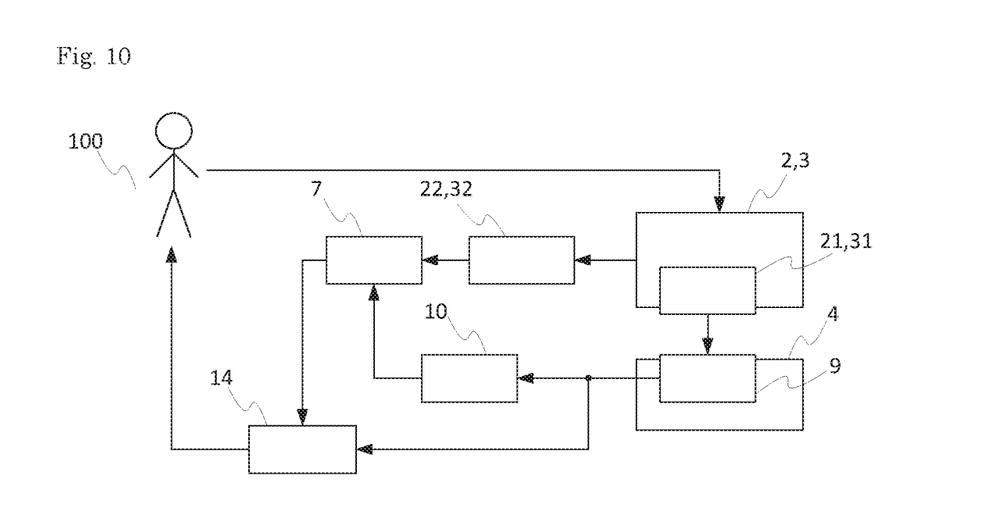
FIG. 10 is a block diagram of the first embodiment.

Next, the system configuration according to the present embodiment will be described with reference to FIG. 10. Each of the first position detector 22 and second position detector 32 is connected to a position measuring unit 7. The position measuring unit 7 measures the amount of positional change based on signals output from the position detectors. In the case that the position detectors are pulse output type incremental encoders, the position measuring unit 7 is configured of a pulse counter. The position measuring unit 7 counts pulses output from the position detectors, measures the magnitude and direction of positional change based on the number of the pulses thereof and phase difference of the two pulse signals at that time, and holds the current relative position as to a reference position.

The rotation regulation detecting unit 9 outputs a signal to the effect that it has been detected that the rotations of the first rotation member 2 and second rotation member 3 are regulated at a predetermined rotation position, to the presentation unit 14 and position information setting unit 10. The result detected at the rotation regulation detecting unit 9 is indicated on the presentation unit 14, thereby informing the user that the rotation members have been positioned in a predetermined position. Also, the current position changed according to the rotations of the first rotation member 2 and second rotation member 3 is informed to the user based on the pulse count of the position measuring unit 7 by the presentation unit 14. A presentation method as to the user may be display of text or audio output. Alternatively, how much the operator has to rotate the first and second rotation members may be presented to him/her instead of the current position. The position information setting unit 10 changes the position information measured and held at the position measuring unit 7 to a predetermined value based on the signal from the rotation regulation detecting unit 9. The predetermined value is equivalent to the original rotation positions of the rotation members 2 and 3 in a state in which both of the rotation members 2 and 3 are positioned by the stopper 4. This predetermined value is assumed to be 0 degrees (origin) in the present embodiment.

Procedure of Home Positioning

Figure 11:
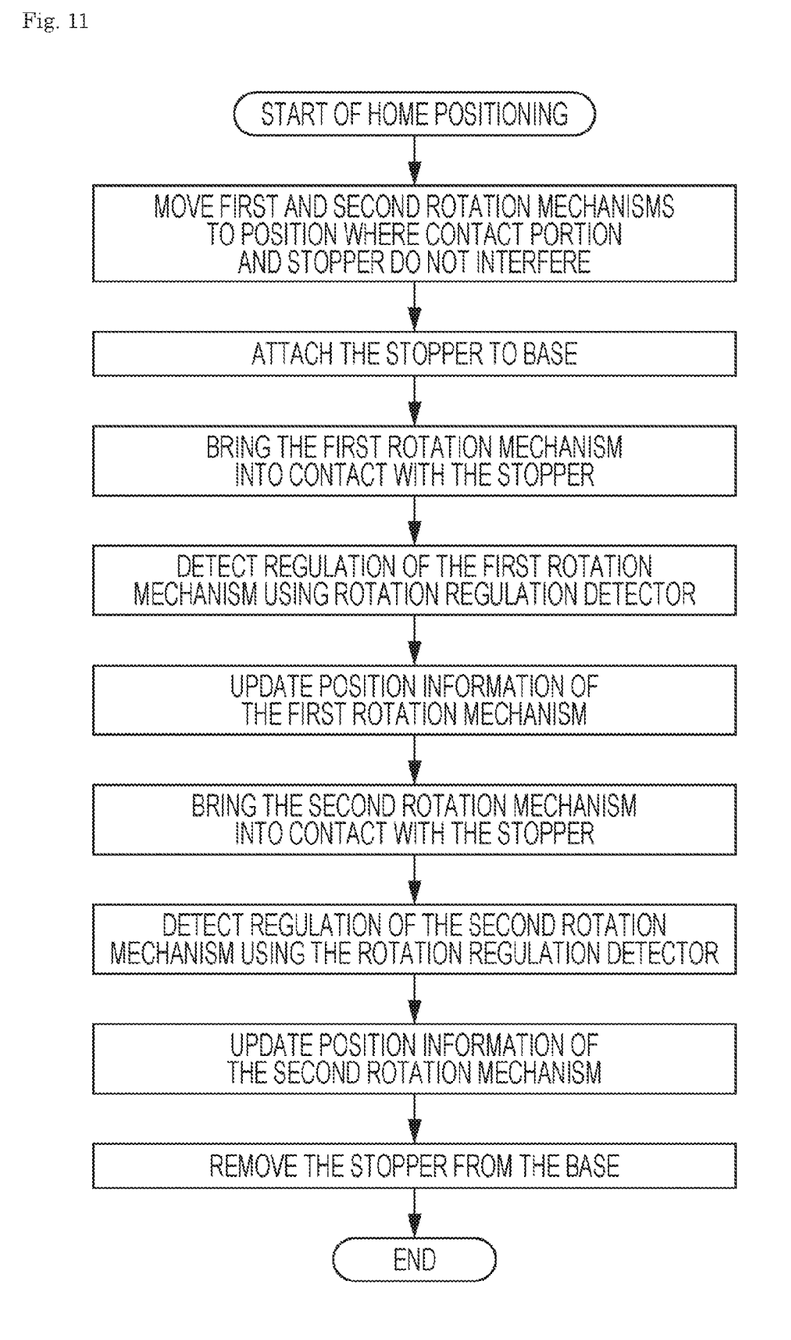
FIG. 11 is a flowchart of the first embodiment.

Next, description will be made regarding a procedure for synchronizing the actual rotation positions of the rotation members with the values of the position detectors, with reference to the flowchart in FIG. 11. As described above, the default values of the position detectors are set to 0 degrees (origin) in the present embodiment.

First, the operator rotates the first rotation member 2 and second rotation member 3 to a position where the first contact portion 21 and second contact portion 31 do not interfere with nor engage with the installed position of the stopper 4. Next, the operator attaches the stopper 4 to the base 1. Next, the operator rotates the first rotation member 2 in the arrow-A direction to engage the first contact portion 21 with the stopper 4. At this time, it is detected that the first contact portion 21 has been engaged with the stopper 4 by the rotation regulation detecting unit 9. Thus, it is indicated on the presentation unit 14 that the first contact portion 21 has been engaged with the stopper 4, and also, the position information of the first rotation member 2 held at the position measuring unit 7 is set to 0 degrees. Next, the operator rotates the second rotation member 3 in the arrow-B direction to engage the second contact portion 31 with the stopper 4. At this time, in the same way as the first contact portion 21 being engaged with the stopper 4, the position information of the second rotation member 3 held at the position measuring unit 7 is set to 0 degrees. Thus, the position information of the first rotation member 2 and second rotation member 3 are synchronized with the actual physical rotation positions (origin) of the first rotation member 2 and second rotation member 3. Also, thereafter, the operator removes the stopper 4 from the base 1, whereby there is no member regulating the rotations of the first rotation member 2 and second rotation member 3. Thus, each of the rotation members is in a 360-degree rotatable state.

According to the above flowchart, there has been employed a mode in which the position information setting unit 10 automatically updates the position information held at the position measuring unit 7 based on the detection signal of the rotation regulation detecting unit 9. However, the method for updating the position information held at the position measuring unit 7 is not restricted to this. For example, an arrangement may be made wherein the position information setting unit 10 is configured of an operation unit such as a switch or the like, the user confirms that the rotation of each rotation member is regulated by the contact portion, and thereafter presses the switch of the position information setting unit 10.

Also, the value that the position information setting unit 10 sets to the position measuring unit 7 has been 0 degrees in the present embodiment. However, the value is not restricted to this. An optional value can be set based on systematic requirements such as a mechanical configuration such as the attachment position of the stopper 4 and so forth, or which position is taken as a reference.

Also, the position measuring unit 7 and position information setting unit 10 may be configured such that the position measuring unit 7 has a function to count pulses, and the position information setting unit 10 has a function to rest the count value thereof.

Second Embodiment

The configuration and operation according to a second embodiment will be described with reference to FIGS. 12 to 18D'. Also, a mechanism for guiding needle-shaped equipment of a medial support apparatus and a method for changing an insertion direction thereof, according to the present embodiment are similar to those in the first embodiment.

External View of Apparatus

The configuration of the mechanism according to the present embodiment will be described with reference to FIGS. 12 to 14. FIG. 14 is a cross-sectional view of the cross section illustrated in FIG. 13 as viewed from an arrow-Y direction. First, there are bases 1a and 1b to be installed onto a puncture target. An annular first rotation member 2 is attached to the base 1b. A first driving source 23 is provided between the base 1b and the first rotation member 2, and the first rotation member 2 is driven by the first driving source 23.

Specifically, the driving source 23 is an annular oscillation type actuator, and is configured of, as illustrated in FIG. 14, a pressurization unit 23a, a piezoelectric element 23b, an oscillation member 23c, and a rotation member 23d. The piezoelectric element 23b excites oscillation based on an applied electric signal. The oscillation member 23c amplifies the oscillation excited by the piezoelectric element 23b as flexural oscillation. Pressure is applied to the oscillation member 23c and rotation member 23d by the pressurization unit 23a, the oscillation of the oscillation member 23c is transmitted to the rotation member 23d by frictional force, and the oscillation member 23c and rotation member 23d are relatively rotated.

The pressurization unit 23a, piezoelectric element 23b, and oscillation member 23c are attached to the first rotation member 2, and the rotation member 23d is fixed to the base 1b. Thus, the first rotation member 2 is rotated on the rotation axis perpendicular to the base 1b by the first driving unit 23.

Also, a second rotation member 3 is installed onto the first rotation member 2. This second rotation member 3 is installed so as to have the rotation axis inclined a predetermined angle against the rotation axis of the first rotation member 2. The second rotation member 3 is assumed to be inclined 15 degrees.

Also, as illustrated in FIG. 14, a second driving source 33 is provided between the first rotation member 2 and second rotation member 3. This second driving source 33 is also provided in the same way as the first driving source 23. Also, the second driving source 33 is configured of, in the same way as the first driving source 23, a pressurization unit 33a, a piezoelectric element 33b, an oscillation member 33c, and a rotation member 33d. The second rotation member 3 is driven by the second driving source 33. Also, a first position detector 22 configured to detect change in the rotation position of the first rotation member 2 as to the base 1b is provided between the base 1b and the first rotation member 2.

Similarly, a second position detector 32 configured to detect change in the rotation position of the second rotation member 3 as to the first rotation member 2 is provided between the first rotation member 2 and the second rotation member 3. The first and second position detectors are both pulse output type incremental encoders.

Also, the second rotation member 3 includes a guide mechanism 50 configured to regulate the insertion direction of needle-shaped equipment 5, which is assumed to have a hole shape in the same way as that in the first embodiment.

Next, a stopper 4 is provided to the base 1b. This stopper 4 has a protruding portion 40 and an elastic member (not illustrated). Later-described FIG. 16C is equivalent to this.

On the other hand, a slot-shaped contact portion is provided to the first rotation member 2 and second rotation member 3 as a first contact portion 21 and a second contact portion 31 respectively, which are engaged with the protruding portion 40 of the stopper 4.

Thus, in the case of having rotated the first rotation member 2 in an arrow-A direction, though the rotation is regulated, the rotation is not regulated in the case of performing inverse rotation against the arrow A. Similarly, the second rotation member 3 is configured so that the rotation is regulated only when being rotated in an arrow-B direction. Thus, the first rotation member 2 and second rotation member 3 can be positioned in a predetermined position.

Figure 13:
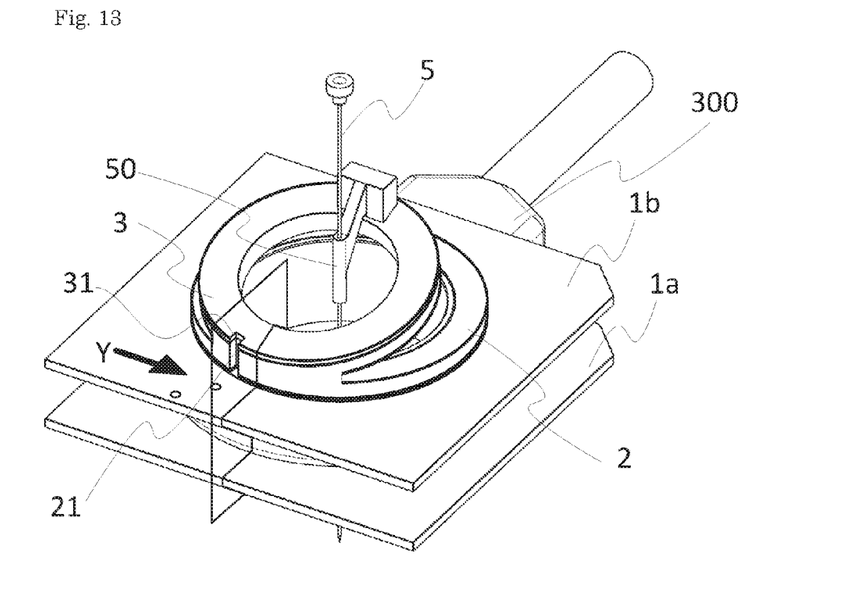
FIG. 13 is a diagram for describing a configuration (state in which the stopper is removed) of the mechanism according to the second embodiment.
Figure 14:
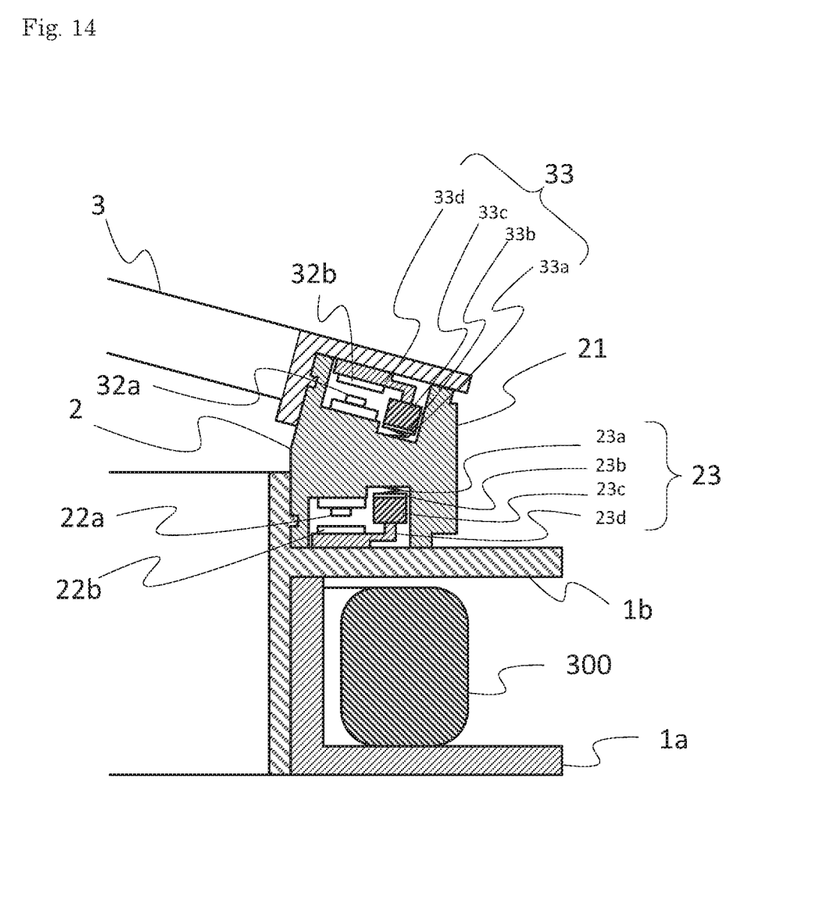
FIG. 14 is a cross-sectional view at the time of a ring Ultrasonic Motor (USM) being mounted.
Figure 16:
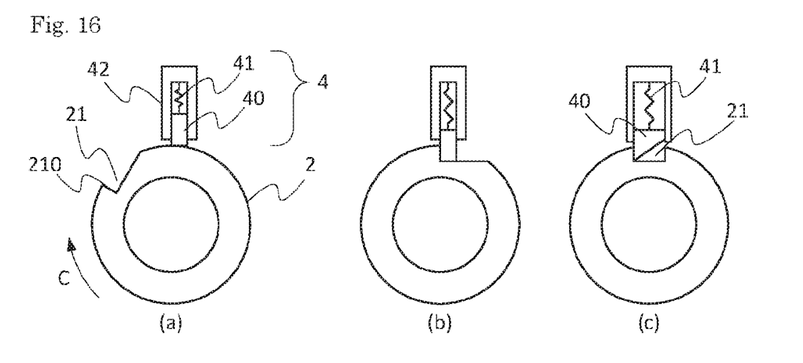
FIGS. 16A to 16C are diagrams for describing another example of the stopper.
Figure 17:
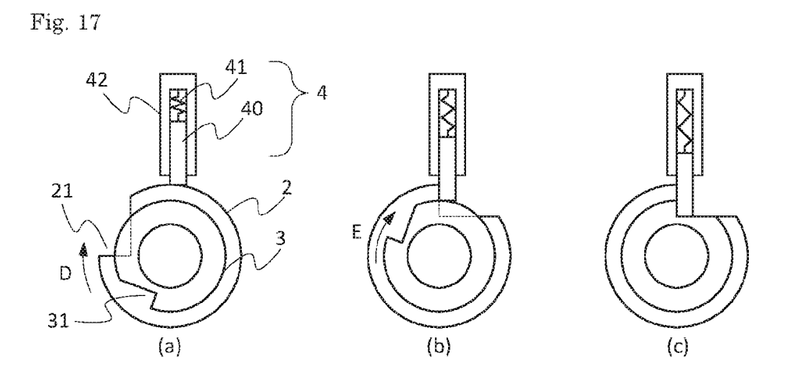
FIGS. 17A to 17C are diagrams for describing another example of the stopper.
Figure 18:
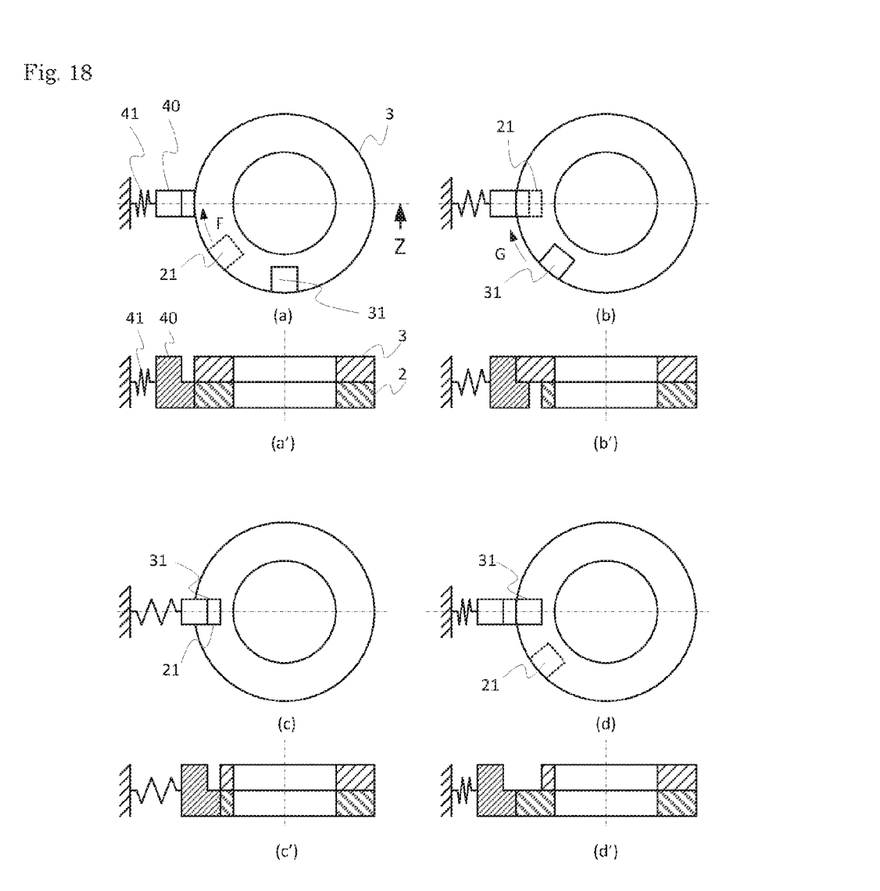
FIGS. 18A to 18D and 18A' to 18D' are diagrams for describing another example of the stopper.

Also, as illustrated in FIG. 13, the stopper 4 is detachable in the present embodiment as well. This detachment suppresses a locus (space) defined by the movement of each of the first and second contact portions and the stopper 4 from crossing on space according to the rotation of each rotation member.

Modification of Stopper

Figure 12:
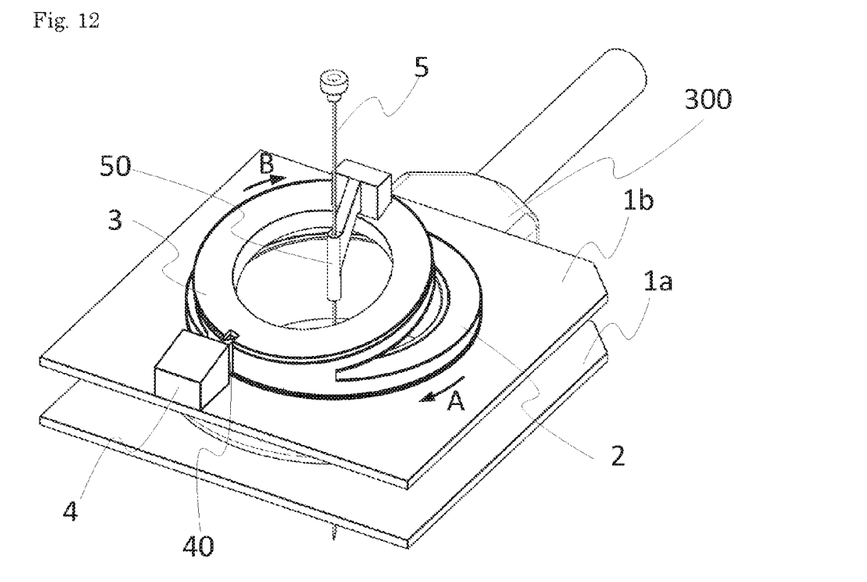
FIG. 12 is a diagram for describing a configuration of a mechanism according to a second embodiment.

The configuration of the stopper 4 according to the present embodiment is not restricted to the configuration described in FIG. 12. The configuration illustrated in FIG. 1 or FIG. 15 may be employed. In this case, in order to stand by for the next driving after home positioning is completed, regulation has to be released by removing the stopper 4 from the base 1b. Note that the home positioning mentioned here means that the rotation position of a rotation member is returned to the home position. Also, in addition to removal, an arrangement may be made wherein a driving source is mounted on the stopper 4, whereby the entire stopper 4 or protruding portion 40 is remotely evacuated to a position where the entire stopper 4 or protruding portion 40 is not in contact with the contact portions 21 and 31. Also, some modifications are assumed even in a mode in which the stopper 4 has a protruding portion and an elastic member as described in FIG. 13. These will be described below with reference to FIGS. 15A to 17C.

FIG. 15A is a rotation member as viewed from above, in which the first rotation member 2 alone is described for simplification of description. An arrangement may be made wherein the contact portion 21 of the rotation member 2 has a recessed shape, and the stopper 4 has a protruding portion 40 which is struck by an elastic member 41 in the diameter direction in the outer circumference of the rotation member 2. In this case, upon the rotation member 2 being rotated and the recessed contact portion 21 reaching the position of the stopper 4, as illustrated in FIG. 15B, the protruding portion 40 of the stopper 4 is inserted into the recessed contact portion 21. Thus, the rotation of the rotation member 2 is regulated. In the case of this configuration, the rotation of the rotation member 2 can be regulated regardless of the rotation direction. Also, in the case of releasing the regulation, pushing back the protruding portion 40 enables the regulation to be released without detaching the entire stopper 4.

Also, the configuration illustrated in FIG. 16A may be employed as another mode of the stopper 4 having the protruding portion 40 and elastic member 41. Difference between this configuration and the configuration in FIGS. 15A and 15B is in that the recessed contact portion 21 provided to the rotation member 2 has an asymmetric shape in the rotation direction of the rotation member 2. Thus, in the case of having rotated the rotation member 2 in an arrow-C direction, as illustrated in FIG. 16B, a contact surface 210 of the contact portion 21 comes into contact with the protruding portion 40 of the stopper 4 to regulate the rotation of the rotation member 2. On the other hand, in the case of having rotated the rotation member 2 in the opposite direction of the arrow C, since the diameter of the rotation member 2 is consecutively increased, and the protruding portion 40 of the stopper 4 does not hang on the contact portion 21, the rotation is not regulated. Also, even in the case of having rotated the rotation member 2 so as to pass through the contact surface 210 of the contact portion 21 in the opposite direction of the arrow C, the protruding portion 40 of the stopper 4 protrudes, which does not regulate the rotation. Also, as illustrated in FIG. 16C, even when the contact portion 21 has a fixed depth, if the protruding portion 40 has a shape having an inclination as to the rotation direction, the same advantage is obtained.

Note that these protruding portion 40 and elastic member 41 do not necessarily have to be provided to the stopper 4, and an arrangement may be made wherein these are provided to the rotation member 2 or 3, and the stopper 4 serves as a contact portion.

Also, FIGS. 17A to 17C illustrate a configuration where the rotations of the two rotation members are regulated by the single stopper 4 having the protruding portion 40 and elastic member 41. FIGS. 17A to 17C are schematically illustrated from the top for convenience of description, assuming that the rotation axis of the first rotation member 2 agrees with the rotation axis of the second rotation member 3. When the first rotation member 2 and second rotation member 3 are in the state in FIG. 17A, the protruding portion 40 of the stopper 4 is in contact with the outer circumference of the first rotation member 2. Upon the first rotation member 2 being rotated in an arrow-D direction from this state, the first contact portion 21 of the first rotation member 2 comes into contact with the protruding portion 40 of the stopper 4 in the position in FIG. 17B, whereby the rotation of the first rotation member 2 is regulated. At this time, the protruding portion 40 of the stopper 4 is in a state adjacent to the outer circumference of the second rotation member 3. Further, upon the second rotation member 3 being rotated in an arrow-E direction, the contact surface of the second contact portion 31 comes into contact with the protruding portion 40 of the stopper 4 in the position in FIG. 17C, whereby the rotation of the second rotation member 3 is regulated. Thus, there may be employed a mechanism in which the rotations of the two rotation members are regulated by the single protruding-shaped stopper 4. Also, in the case of usage that does not interfere with a movable range of a rotation member, the stopper 4 may be installed permanently and have a shape incapable of detachment and evacuation.

Finally, FIGS. 18A to 18D and 18A' to 18D' illustrate a different configuration wherein the rotations of the two rotation members are regulated by the single stopper 4 including the protruding portion 40 and elastic member 41. FIGS. 18A to 18D and 18A' to 18D' are schematically illustrated for convenience of description, assuming that the rotation axis of the first rotation member 2 agrees with the rotation axis of the second rotation member 3, and the outer radiuses of both rotation members are equal. FIGS. 18A to 18D represent top views, and FIGS. 18A' to 18D' represent cross-sectional views as cross sections illustrated by dashed-dotted lines in FIGS. 18A to 18D viewed from an arrow-Z side.

A feature of the present embodiment is, as illustrated in FIG. 18A', in that the length of the protruding portion 40 differs between a portion thereof which is in contact with the first rotation member 2 and a portion thereof which is in contact with the second rotation member 3. When the first rotation member 2 and second rotation member 3 are in the state in FIG. 18A, the protruding portion 40 of the stopper 4 is in contact with the outer circumference of the first rotation member 2. Upon the first rotation member 2 being rotated in an arrow-F direction from this state, the first contact portion 21 of the first rotation member 2 comes into contact with the protruding portion 40 of the stopper 4 in the position in FIG. 18B, whereby the rotation of the first rotation member 2 is regulated. At this time, the protruding portion 40 of the stopper 4 is in contact with the outer circumference of the second rotation member 3.

Further, upon the second rotation member 3 being rotated in an arrow-E direction, the contact surface of the second contact portion 31 comes into contact with the protruding portion 40 of the stopper 4 in the position in FIG. 18C, whereby the rotation of the second rotation member 3 is regulated.

Also, even if the protruding portion 40 of the second rotation member 3 is rotated at a position which is in contact with the protruding portion 40 from the state in FIG. 18A, the protruding portion 40 is not inserted into the contact portion 31, since the first rotation member 2 is in contact with the protruding portion 40, as illustrated in FIG. 18D'. Thus, a configuration can be realized in a sure manner wherein after the first rotation member 2 is positioned, the second rotation member 3 is positioned.

System Block Diagram

Figure 19:
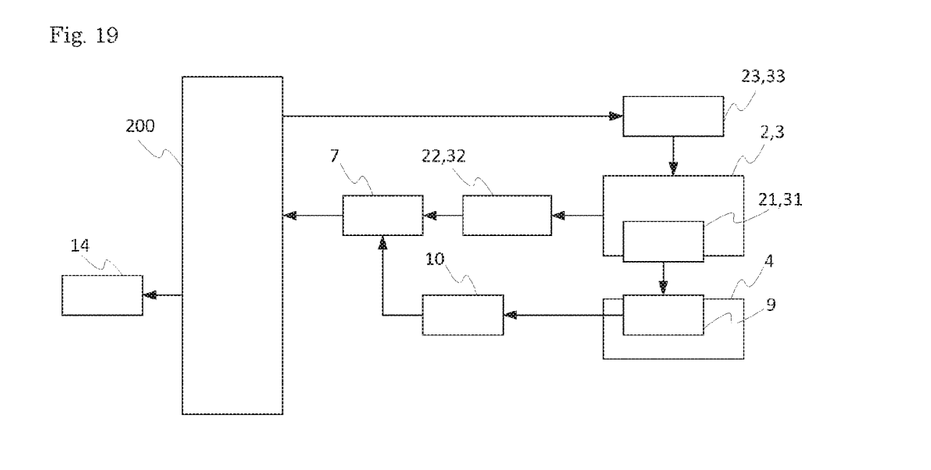
FIG. 19 is a block diagram of the second embodiment.

The system configuration according to the present embodiment will be described with reference to FIG. 19. First, a controller 200 is connected to the first driving source 23 and second driving source 33. The controller 200 includes a central processing unit (CPU) 201, read only memory (ROM) 202, random access memory (RAM) 203, and a driving circuit 205. These units are connected by a bus. The CPU 201 is configured to execute various types of processing with the RAM 203 as a work area based on instruction code stored in the ROM 202. The two driving sources are driven based on a command from the controller 200 (driving circuit 205), and accordingly, the first rotation member 2 and second rotation member 3 are rotated.

The first position detector 22 and second position detector 32 are each connected to the position measuring unit 7. The position measuring unit 7 measures and holds the change amount of the positions of the first rotation member 2 and second rotation member 3 based on a signal output from a position detector. The signal output here is assumed to be the same as that in the first embodiment. The controller 200 control the driving sources based on this position information.

The rotation regulation detecting unit 9 detects that the rotations of the first rotation member 2 and second rotation member 3 are regulated in a predetermined rotation position, and outputs a signal indicating detection thereof to the position information setting unit 10. The rotation regulation detecting unit 9 according to the present embodiment includes the photo interrupter 91 illustrated in FIG. 9.

The position information setting unit 10 changes the position information measured and held at the position measuring unit 7 into a predetermined value based on the signal from the rotation regulation detecting unit 9. This predetermined value is assumed to be 0 degrees in the present embodiment.

Also, the controller 200 presents information regarding the rotation position and drive of each rotation member on the presentation unit 14.

A procedure for synchronizing the actual rotation positions of the rotation members according to the present embodiment with the values of position detectors is the same as that in the first embodiment except that driving of the rotation members is performed by the driving sources 23 and 33 instead of the hand, and also detachment of the stopper 4 is not needed. As described above, the home position of the mechanism and the position information of the encoders can be synchronized in a sure manner even with the configuration including the driving sources.

Modification

Guide Mechanism 50

The guide mechanism 50 is configured of a detachable/mountable holder type as to the rotation member 3, whereby ease of use for the needle guiding apparatus can further be improved.

Stopper 4

Figure 20:
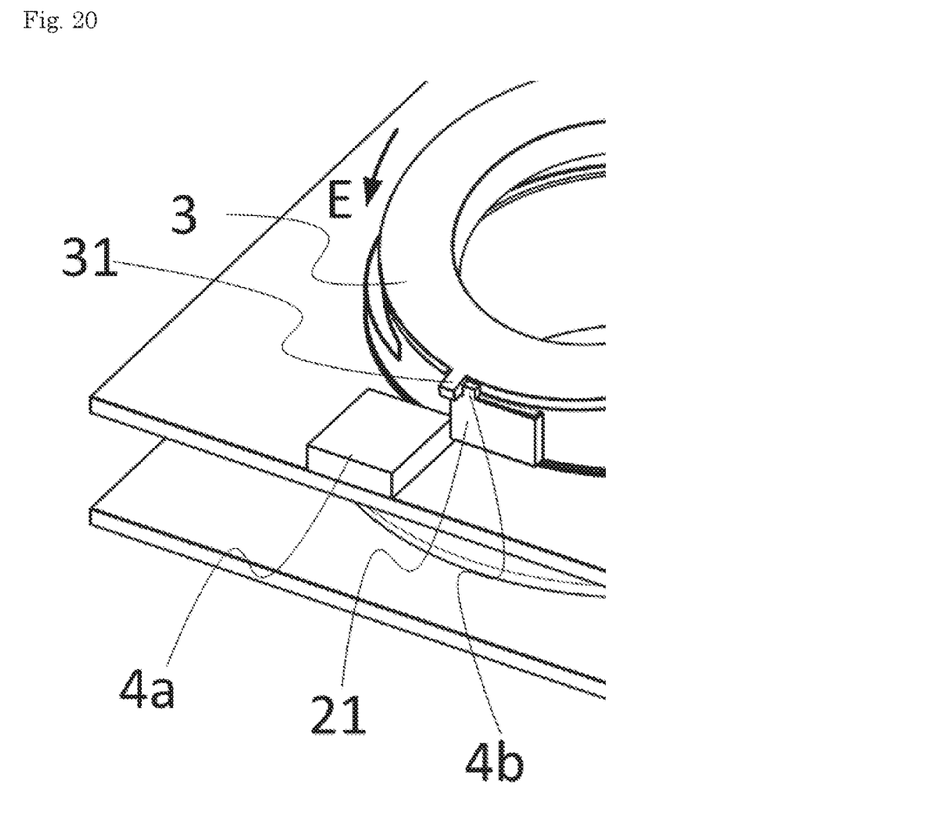
FIG. 20 is a diagram for describing a configuration example with two stoppers.

Though the single stopper 4 is provided to the base 1, and regulation for the rotations of the two rotation members is performed in the above embodiments, a different stopper 4 may be provided to each of the first rotation member 2 and second rotation member 3, for example. Specifically, as illustrated in FIG. 20, an arrangement may be made wherein a stopper 4a provided to the base 1 regulates the rotation of the first rotation member 2 alone. Next, the rotation of the second rotation member 3 is regulated by rotating the second rotation member 3 from an arrow-E direction to be brought into contact with a second stopper 4b provided to the first rotation member 2. Though the second stopper 4b is provided onto the contact portion 21 of the first rotation member 2 as the example in FIG. 20, the position of the second stopper 4b is not restricted to this. The second stopper 4b may be independently provided to another place of the first rotation member 2, or may be detachable.

Rotation Regulation Detecting Unit 9

Also, though the rotation regulation detecting unit 9 has a configuration with a sensor in the above embodiments, the dedicated sensor does not necessarily have to be used. For example, an arrangement may be made wherein a driving source is driven with fixed torque, and the output of the position detecting unit at that time is monitored. Specifically, though a pulse is output from the position detecting unit with a predetermined interval while the rotation is not regulated, upon the rotation being regulated, the output of a pulse is stopped. Therefore, regulation of the rotation can be detected without employing a dedicated sensor by detecting that the pulse width reaches equal to or wider than a predetermined value.

Also, additionally, controlling the driving source at fixed speed based on the position detecting unit increases a torque command to the driving source in comparison with a normal state when the rotation is regulated, and accordingly, regulation of the rotation can also be detected by detecting increase in the torque command.

Driving Sources 22 and 23

Also, though an example with the annular oscillation type actuator has been described in the above embodiments, a driving source may be provided onto the outer circumferential sides of the rotation members 2 and 3 regardless of the method for implementing the driving source, for example. Also, though an example with the oscillation type actuator has been described in the above embodiments, a pneumatic actuator is also assumed to be used in that this actuator is suitable for usage within an MRI environment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A positioning apparatus comprising:
   a guide configured to guide needle-shaped medical equipment in a longitudinal direction of the needle-shaped medical equipment;
   a ring-shaped rotation unit having an inner circumference and an outer circumference and configured to rotate around its rotation axis to direct the needle-shaped medical equipment to an insertion direction not parallel to the rotation axis, the ring-shaped rotating unit holding the guide inside the inner circumference and having a contact portion along the outer circumference;
   a detector configured to detect a change in a rotation position of the rotation unit and to output a corresponding signal;
   a position measuring unit configured to measure an amount of rotation and output position information of the rotation unit based on the signal output by the detector;
   a stopper which is removably engageable with the contact portion of the rotation unit and configured to regulate the rotation of the rotation unit so as to stop movement of the guide; and
   a setting unit configured to set the position information to a value corresponding to a predetermined position.

2. The positioning apparatus according to claim 1, further comprising a base,
   wherein the rotation unit includes a first rotation member, and a second rotation member;
   wherein the first rotation member is fixed to the base;
   wherein the second rotation member is mounted on the first rotation member; and
   wherein the stopper is configured to stop rotation of at least one of the first and second rotation members.

3. The positioning apparatus according to claim 2,
   wherein each of the first rotation member and the second rotation member includes a contact member; and
   wherein the stopper is engageable with the two contact members, thereby regulating the rotations of the first rotation member and the second rotation member.

4. The positioning apparatus according to claim 3, further comprising:

a first driving source configured to drive the first rotation member;
a second driving source configured to drive the second rotation member; and
a controller,
wherein the controller controls the first driving source and the second driving source so as to engage the contact member of the second rotation member with the stopper after engaging the contact member of the first rotation member with the stopper.

5. The positioning apparatus according to claim 2, wherein each of the first rotation member and the second rotation member includes a recessed contact member;
wherein the stopper includes a protruding portion;
wherein the protruding portion includes
a first portion which is in contact with the contact member of a single rotation member which is either of the first or second rotation members, and
a second portion which is in contact with the contact member of the other rotation member different from the rotation member with which the first portion is in contact;
wherein, in a state in which the first portion is in contact with the single rotation member, and is also not engaged with the contact member of the single rotation member the second portion is not in contact with the contact member of the other rotation member; and
wherein, in a state in which the first portion is inside of the single rotation member in a radial direction, and is also engaged with the contact member of the single rotation member, the second portion is in contact with the contact member of the other rotation member.

6. The positioning apparatus according to claim 1, further comprising:
a driving source configured to drive the rotation unit.

7. The positioning apparatus according to claim 6,
wherein the driving source is a piezoelectric actuator.

8. The positioning apparatus according to claim 1, wherein the stopper is movable so that the stopper does not intersect with a locus on a space of the contact portion defined by the rotation of the rotation unit.

9. The positioning apparatus according to claim 1, further comprising:
a rotation regulation detecting unit configured to detect that the rotation of the rotation unit is regulated by the contact portion and the stopper;
wherein the setting unit sets the value as the position information according to detection of the rotation regulation detecting unit.

10. The positioning apparatus according to claim 1,
wherein the contact portion is a protruding portion of the outer circumference extending outwardly in a radial direction.

11. The positioning apparatus according to claim 1,
wherein the contact portion is a slotted portion of the outer circumference extending inwardly in a radial direction, and
wherein the stopper includes a protruding portion configured to removably engage with the slotted portion.

12. The positioning apparatus according to claim 1, further comprising a base,
wherein the rotation unit includes a first rotation member, and a second rotation member;
wherein the first rotation member is integrally fixed to the base, and the second rotation member is mounted on the first rotation member;
wherein the stopper is removably attached to the base; and
wherein the stopper is configured to removably engage with at least one of the first and second rotation members to regulate the rotation of the rotation unit.

13. The positioning apparatus according to claim 1, further comprising a base,
wherein the rotation unit includes a first rotation member, and a second rotation member;
wherein the first rotation member is integrally fixed to the base, and the second rotation member is mounted on the first rotation member; and
wherein a rotation axis of the second rotation member is inclined at a predetermined angle with respect to a rotation axis of the first rotation member.

14. The positioning apparatus according to claim 13,
wherein rotation of the second rotation member with respect to the first rotation member changes the insertion direction of the needle-shaped medical equipment.

15. The positioning apparatus according to claim 14,
wherein, in a case of rotating the second rotation member by 180 degrees with respect to the first rotation member, the value of an insertion angle of the needle-shaped medical equipment is doubled.

16. The positioning apparatus according to claim 1, further comprising a base,
wherein the rotation unit is integrally fixed to the base, and
wherein the stopper is removably mounted to the base.

17. The positioning apparatus according to claim 16,
wherein the base includes one or more holes; and
wherein the stopper includes one or more pins configured to removably engage and disengage with the one or more holes.

18. The positioning apparatus according to claim 16,
wherein the base includes a linear recessed portion,
wherein the stopper includes a linear ridge configured to removably engage and disengage with the linear recessed portion.

19. The positioning apparatus according to claim 1,
wherein the outer circumference of the rotation unit includes a slotted portion as the contact portion,
wherein the stopper includes a protruding portion configured to removably engage with the slotted portion, and
wherein the protruding portion of the stopper engages with the slotted portion of the rotation unit regardless of a rotation direction of the rotation unit.

20. The positioning apparatus according to claim 1,
wherein the outer circumference of the rotation unit includes a slotted portion as the contact portion,
wherein the stopper includes a protruding portion configured to removably engage with the slotted portion, and
wherein the protruding portion of the stopper engages with the slotted portion of the rotation unit in only one rotation direction of the rotation unit.

21. The positioning apparatus according to claim 1,
wherein the stopper engages with the contact portion of the rotation unit prior to stopping rotation thereof and the setting unit sets the position information to a value corresponding to the predetermined position after the stopper stops the rotation of the rotation unit at the predetermined position.

* * * * *